(12) United States Patent
Bate et al.

(10) Patent No.: US 7,276,596 B2
(45) Date of Patent: Oct. 2, 2007

(54) PROMOTER FROM MAIZE INVERTASE INHIBITOR GENE

(75) Inventors: Nicholas J. Bate, Urbandale, IA (US); Odd Arne Olsen, Johnston, IA (US); Timothy G. Helentjaris, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 519 days.

(21) Appl. No.: 10/786,679

(22) Filed: Feb. 25, 2004

(65) Prior Publication Data
US 2004/0210960 A1 Oct. 21, 2004

Related U.S. Application Data

(60) Provisional application No. 60/450,128, filed on Feb. 25, 2003.

(51) Int. Cl.
*C12N 15/82* (2006.01)
*C07H 21/04* (2006.01)
*A01H 5/00* (2006.01)

(52) U.S. Cl. ............ 536/24.1; 800/287; 800/298; 435/468; 435/419; 435/320.1

(58) Field of Classification Search ............ None
See application file for complete search history.

(56) References Cited

U.S. PATENT DOCUMENTS 6,713,666 B2 3/2004 Helentjaris et al.

FOREIGN PATENT DOCUMENTS

| WO | WO 01/16340 | * | 3/2001 |
|----|-------------|---|--------|
| WO | WO 01/25439 A1 | | 4/2001 |
| WO | WO 02/36788 A2 | | 5/2002 |

OTHER PUBLICATIONS

Kim et al. A 20 nucleotide upstream element is essential for the nopaline synthase (nos) promoter activity. (1994) PMB, vol. 24, pp. 105-117.*
Maiti et al. Promoter/leader deletions analysis and plant expression vectors with the figwort mosaic virus (FMV) full length transcript (FLt) promoter containing single or double enhancer domains. (1997) Transgenic Research, vol. 6, pp. 143-156.*
Bonello et al. Esr genes show different levels of expression in the same region of maize endosperm. (2000) Gene, vol. 246, pp. 219-227.*
Bonello, J-F, et al.; "Esr genes show different levels of expression in the same region of maize endosperm"; Gene 246 (2000) 219-227.
Opsahl-Ferstad, H-G, et al.; "ZmEsr, a novel endosperm-specific gene expressed in a restricted region around the maize embryo"; The Plant Journal (1997) 12(1) 235-246.
Bate, N., et al.; "An Invertase Inhibitor from Maize Localizes to Embryo Surrounding Region during Early Kernel Development"; Plant Physiology, Jan. 2004, vol. 134, pp. 246-254.
Sharma, V.K., et al.; The Arabidopsis CLV3-like (CLE) genes are expressed in diverse tissues and encode secreated proteins; Plant Molecular Biology 51:415-425, 2003.

* cited by examiner

*Primary Examiner*—Anne Kubelik
*Assistant Examiner*—Cathy Kingdon Worley

(57) ABSTRACT

The present invention provides compositions and methods for regulating expression of heterologous nucleotide sequences in a plant. Compositions include a novel nucleotide sequence for a tissue-preferred promoter for the *Zea mays* gene encoding INVINH1. A method for expressing a heterologous nucleotide sequence in a plant using the promoter sequences disclosed herein is provided. The method comprises stably incorporating into the genome of a plant cell a polynucleotide operably linked to the promoter of the present invention and regenerating a stably transformed plant that expresses the linked polynucleotide.

29 Claims, 1 Drawing Sheet

Figure 1: In situ localization of InvINH1 transcript. Expression of InvINH1 is localized to the ESR of 5DAP kernels.
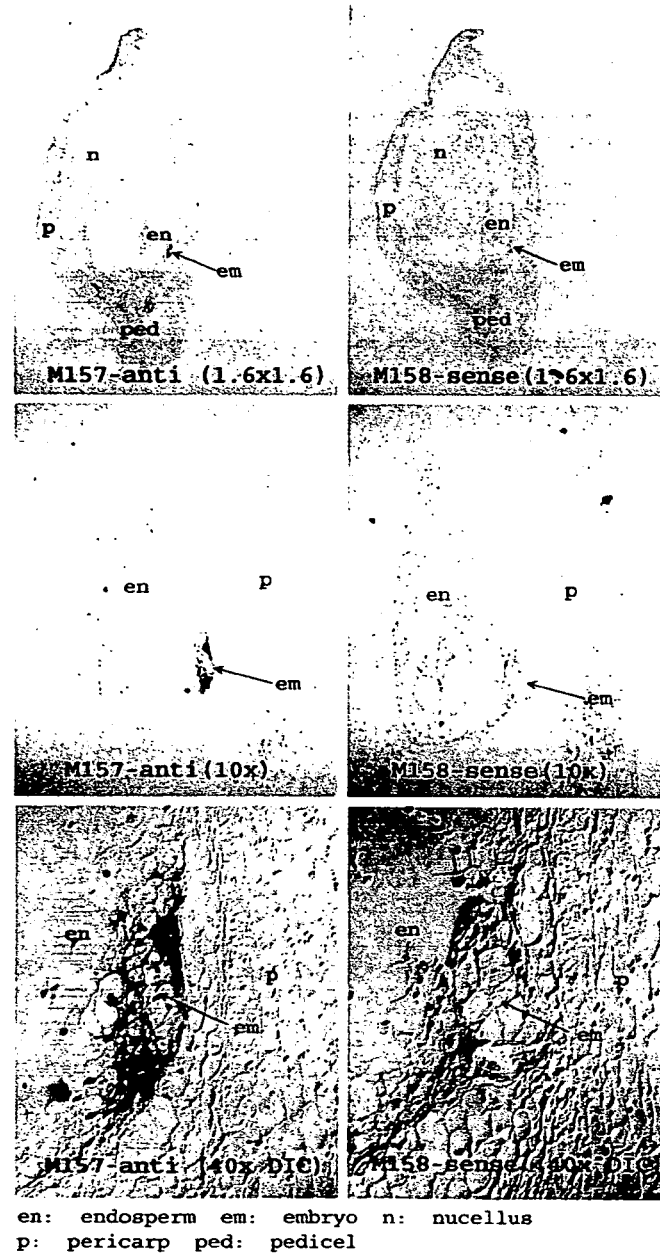
en: endosperm  em: embryo  n: nucellus
p: pericarp  ped: pedicel

SEQUENCE LISTING

```
<160> NUMBER OF SEQ ID NOS: 3

<210> SEQ ID NO 1
<211> LENGTH: 590
<212> TYPE: DNA
<213> ORGANISM: Zea mays
<220> FEATURE:
<221> NAME/KEY: misc_feature
<222> LOCATION: (588)...(590)
<223> OTHER INFORMATION: Start Codon for INVINH1 gene.

<400> SEQUENCE: 1
```

```
gaattcgccc ttggtagatg tctagatgac ctattctact tttcctaaga ttttctctgt    60
atgagtaacc tgtcataatt taacttgtga gatcttgccg atataaaaaa aaaacgccag   120
tcatttatgg tacgggatta ataggttcca agaaccagcc acaatccatt tattagtttc   180
atataaatgt cataaatttt tactaaaatt ttctctgtat agtaacatgt cataactgaa   240
cttgtgagaa aaacgccagt tatttatggt acgggattaa taggttccaa aaaccagccg   300
taacctattt atattagggt actttaagct ggtgccctca gttttgttgg tgtcttcgtt   360
tttaaactta gttgtatttt ttttcttagt tctgtccttc tagtgttata gagcataagg   420
acaaaattga gcaaaaaatg actaaggata aaaatgagga tatcagaaag ggcagcagct   480
taaaaaacct tttatattag ttcaaaagga caccagtcta taaaaagtat actccaagca   540
catttgaatt tggatttgca ttgtcagtca ggccagtcaa ggggaccatg              590

<210> SEQ ID NO 2
<211> LENGTH: 30
<212> TYPE: DNA
<213> ORGANISM: Artificial Sequence
<220> FEATURE:
<223> OTHER INFORMATION: PCR primer

<400> SEQUENCE: 2
aacttgatgc agtaggcgta gccggtgtcc                                     30

<210> SEQ ID NO 3
<211> LENGTH: 30
<212> TYPE: DNA
<213> ORGANISM: Artificial Sequence
<220> FEATURE:
<223> OTHER INFORMATION: PCR primer

<400> SEQUENCE: 3
cttgtaggac ggaagcgttg gacgtggagc                                     30
```

PROMOTER FROM MAIZE INVERTASE INHIBITOR GENE

This application claims the benefit of, and hereby incorporates by reference, provisional patent application 60/450,128, filed Feb. 25, 2003.

FIELD OF THE INVENTION

The present invention relates to the field of plant molecular biology, more particularly to regulation of gene expression in plants.

BACKGROUND OF THE INVENTION

The kernel of the maize plant, Zea mays, consists of four separate components: the pericarp, or hull, which is the outer covering of the kernel; the germ, or plant embryo; the endosperm, which makes up over 80% of the kernel and which provides energy and protein for the developing embryo; and, the tip cap, which is the attachment point of the kernel to the corncob. Of these components, the endosperm is particularly important because the starch and protein reserves it contains are a major source of food, feed, and industrial raw material, a fact which is true not just for corn, but for cereal plants in general.

Cereal endosperm is generally divided into four major regions with clearly distinct functions: the starchy endosperm, which takes up most of the volume, is a storage organ accumulating reserve substances; the aleurone layer, which is the outer cell layer surrounding the endosperm, stays alive during seed dormancy and is essential for the mobilization of the reserve substances during germination; the basal endosperm transfer layer, which is a specialized part of the outer cell layer in close contact with the vascular bundles of the mother plant, is responsible for high throughput nutrient transfer from source organs into the developing endosperm; and, the embryo surrounding region ("ESR"), which is characterized by small cells rich in cytoplasm, which possibly extends the functions of the suspensor in embryo nutrition. See Bonello et al. (2000) Gene 246:219-227, the contents of which are herein incorporated by reference.

Given the agronomic importance of the endosperm, there is a continued need for techniques for improving the composition or development of this tissue or one of its component regions. One such technique involves the use of expression constructs that comprise a promoter that drives expression of operably linked endogenous or exogenous genes of interest preferentially in the endosperm or one of its component regions. With regard to the ESR region, for example, the ESR-preferred expression of an endogenous or exogenous protein controlling cell division (e.g., a cytokinin biosynthesis gene such as isopentenyl transferase) could be used to increase the number of cells in the ESR, possibly resulting in larger seeds or creating a sink for photosynthate to buffer seed development during transient abiotic stress. Preferential expression of a protein of interest in a particular region of the endosperm may also be useful for affecting surrounding regions. For example, preferential expression in the ESR of genes that are toxic or deleterious to the adjacent embryo (e.g., DAM methylase from E. coli) could be used to damage or destroy the embryo. Additionally, the ESR-preferred expression of an antisense RNA sequence may be used to inhibit the expression of endogenous genes, thereby modulating the development or altering the composition of the endosperm.

In light of the above discussion, it is clear that there is a significant need for plant regulatory elements that preferentially direct gene expression to the endosperm or one of its component regions. The present invention satisfies this need by providing a promoter with activity that is specific to the ESR region of endosperm, that is, an ESR-preferred promoter.

SUMMARY OF THE INVENTION

Compositions and methods for regulating gene expression in a plant are provided. Compositions comprise a novel nucleotide sequence for a promoter that initiates transcription in an ESR-preferred manner. More particularly, the transcriptional initiation region controlling expression of the maize invertase inhibitor gene INVINH1 is provided as the nucleotide sequence set forth in SEQ ID NO:1. The compositions of the invention further comprise nucleotide sequences having at least 70% sequence identity to the sequence set forth in SEQ ID NO:1, as well as operable fragments of SEQ ID NO:1. Other embodiments are partial or full-length nucleotide sequences that hybridize under stringent conditions to the sequence set forth as SEQ ID NO:1, or to its complement.

Compositions of the present invention also include expression cassettes comprising a promoter of the invention operably linked to a polynucleotide of interest. The invention further provides expression vectors, and plants or plant cells having stably incorporated into their genomes an expression cassette mentioned above. Additionally, compositions include transgenic seed of such plants.

Methods of the invention comprise a means for selectively expressing a polynucleotide in a plant seed, particularly in the embryo surrounding region of a plant seed. The methods comprise transforming a plant cell with an expression cassette and regenerating a transformed plant from this plant cell, where the expression cassette comprises a promoter of the invention and a polynucleotide of interest operably linked to this promoter, wherein the promoter initiates ESR-preferred transcription of the operably linked polynucleotide in the embryo surrounding region of transformed seed of the transformed plant. In this manner, the promoter sequences are useful for controlling the expression of operably linked coding sequences in an ESR-preferred manner, thereby effecting useful changes in the phenotype of a seed of the transformed plant.

Downstream from and under the transcriptional initiation regulation of the promoter will be a polynucleotide of interest that will provide for modification of the phenotype of the seed of the transformed plant. Such modification includes modulating the production of an endogenous product as to amount, relative distribution, or the like, or production of an exogenous expression product to provide for a novel function or product in the seed of the transformed plant.

The following embodiments are encompassed by the present invention:

1. An isolated nucleic acid molecule comprising a polynucleotide represented by a sequence selected from the group consisting of:
   a) SEQ ID NO:1, or a complement thereof;
   b) at least 55 contiguous nucleotides of SEQ ID NO:1, wherein said polynucleotide initiates transcription in a plant cell;
   d) a nucleotide sequence having at least 70% sequence identity to SEQ ID NO:1, wherein said polynucleotide initiates transcription in a plant cell;

e) a sequence representing a polynucleotide that hybridizes under stringent conditions to the full-length complement of SEQ ID NO:1, wherein said polynucleotide initiates transcription in a plant cell.

2. An expression cassette comprising a nucleic acid molecule of embodiment 1 operably linked to a polynucleotide of interest.

3. A vector comprising the expression cassette of embodiment 2.

4. A plant cell having stably incorporated into its genome the expression cassette of embodiment 2.

5. The plant cell of embodiment 4, wherein said plant cell is from a monocot.

6. The plant cell of embodiment 5, wherein said monocot is maize, barley, wheat, oat, rye, sorghum, or rice.

7. A plant having stably incorporated into its genome the expression cassette of embodiment 2.

8. The plant of embodiment 7, wherein said plant is a monocot.

9. The plant of embodiment 8, wherein said monocot is maize, barley, wheat, oat, rye, sorghum, or rice.

10. A transgenic seed of the plant of embodiment 7.

11. The plant of embodiment 7, wherein the polynucleotide of interest encodes a gene product that confers pathogen or insect resistance.

12. The plant of embodiment 7, wherein the polynucleotide of interest encodes a polypeptide involved in cell cycle regulation, carbohydrate metabolism, protein metabolism, fatty acid metabolism, or phytohormone biosynthesis.

13. A method for expressing a first polynucleotide in a plant, said method comprising introducing into a plant an expression cassette comprising a promoter and a first polynucleotide operably linked thereto, wherein said promoter comprises a second polynucleotide that initiates transcription of an operably linked polynucleotide in a plant cell, and wherein said second polynucleotide is represented by a sequence selected from the group consisting of:
   a) SEQ ID NO:1, or a complement thereof;
   b) at least 55 contiguous nucleotides of SEQ ID NO:1;
   c) a sequence at least 70% sequence identical to SEQ ID NO:1; and
   d) a sequence representing a polynucleotide that hybridizes under stringent conditions to the full-length complement of SEQ ID NO:1.

14. The method of embodiment 13, wherein said first nucleotide sequence is selectively expressed in the embryo surrounding region.

15. The method of embodiment 13, wherein said plant is a monocot.

16. The method of embodiment 15, wherein said monocot is maize, barley, wheat, oat, rye, sorghum, or rice.

17. The method of embodiment 13, wherein said first polynucleotide encodes a gene product that confers pathogen or insect resistance.

18. The method of embodiment 13, wherein said first polynucleotide encodes a polypeptide involved in cell cycle regulation, carbohydrate metabolism, protein metabolism, fatty acid metabolism, or phytohormone biosynthesis.

19. A method for expressing a first polynucleotide in a plant cell, said method comprising introducing into a plant cell an expression cassette comprising a promoter and a first polynucleotide operably linked thereto, wherein said promoter comprises a second polynucleotide that initiates transcription of an operably linked polynucleotide in a plant cell, and wherein said second polynucleotide is represented by a sequence selected from the group consisting of:
   a) SEQ ID NO:1, or a complement thereof;
   b) at least 55 contiguous nucleotides of SEQ ID NO:1;
   c) a sequence at least 70% identical to SEQ ID NO:1; and,
   d) a sequence representing a polynucleotide that hybridizes under stringent conditions to the complement of SEQ ID NO:1.

20. The method of embodiment 19, wherein said plant cell is from a monocot.

21. The method of embodiment 20, wherein said monocot is maize, barley, wheat, oat, rye, sorghum, or rice.

22. The method of embodiment 19, wherein said first polynucleotide encodes a gene product that confers pathogen or insect resistance.

23. The method of embodiment 19, wherein said first polynucleotide encodes a polypeptide involved in cell cycle regulation, carbohydrate metabolism, protein metabolism, fatty acid metabolism, or phytohormone biosynthesis.

24. A method for selectively expressing a first polynucleotide in the embryo surrounding region (ESR) of a plant seed, said method comprising introducing into a plant an expression cassette comprising a promoter and a first polynucleotide operably linked thereto, wherein said promoter comprises a second polynucleotide that initiates transcription of an operably linked polynucleotide in the ESR of a plant seed, and wherein said second polynucleotide is represented by a nucleotide sequence selected from the group consisting of:
   a) SEQ ID NO:1, or a complement thereof;
   b) at least 55 contiguous nucleotides of SEQ ID NO:1;
   c) a sequence at least 70% identical to SEQ ID NO:1; and,
   d) a sequence representing a polynucleotide that hybridizes under stringent conditions to the complement of SEQ ID NO:1.

25. The method of embodiment 24, wherein expression of said first polynucleotide alters the phenotype of said transformed seed.

26. The method of embodiment 24, wherein the plant is a monocot.

27. The method of embodiment 26, wherein the monocot is maize, barley, wheat, oat, rye, sorghum, or rice.

28. The method of embodiment 24, wherein the first polynucleotide encodes a gene product that confers pathogen or insect resistance.

29. The method of embodiment 24, wherein the first polynucleotide encodes a polypeptide involved in cell cycle regulation, carbohydrate metabolism, protein metabolism, fatty acid metabolism, or phytohormone biosynthesis.

BRIEF DESCRIPTION OF THE DRAWINGS

FIG. 1 provides the in situ hybridization results showing the expression pattern of the INVINH1 gene in maize ESR for kernels 5 DAP (days after pollination).

DETAILED DESCRIPTION OF THE INVENTION

The compositions of the present invention comprise novel isolated polynucleotides comprising plant promoters, particularly an "ESR-preferred" promoter isolated from the maize invertase inhibitor gene INVINH1 described in co-pending U.S. patent application Ser. No. 09/780,717, filed Feb. 9, 2001. (See also Bate, N., et al., Plant Physiol. 134(1):246-254 (2004)) In particular, the present invention provides for isolated nucleic acid molecules comprising the INV1NH1 promoter as described by the nucleotide sequence set forth in SEQ ID NO:1, and fragments, variants, and complements thereof.

The promoter sequences of the invention are useful for expressing operably linked polynucleotides in a plant in a tissue-preferred manner, particularly an ESR-preferred manner. The sequences of the invention also find use in the construction of expression vectors for subsequent transformation into plants of interest, as probes for the isolation of other INVINH1-like genes, as molecular markers, and the like.

The invention encompasses isolated or substantially purified nucleic acid molecule compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The compositions of the invention include isolated nucleic acid molecules comprising the maize INVINH1 promoter as set forth in SEQ ID NO:1. By "promoter" is intended a regulatory region of DNA usually comprising a TATA box capable of directing RNA polymerase II to initiate transcription (i.e., RNA synthesis) at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements such as those responsible for tissue and temporal expression of the coding sequence, enhancers, and the like. See particularly Australian Patent No. AU-A-77751/94 and U.S. Pat. Nos. 5,466,785 and 5,635,618. In the same manner, the promoter elements that enable expression in the desired tissue such as the ESR can be identified, isolated, and used with other core promoters to confer ESR-preferred expression. By "core promoter" is intended a promoter that contains the essential nucleotide sequences for expression of an operably linked polynucleotide, and includes the TATA box and start of transcription. By this definition, a core promoter may or may not have detectable activity in the absence of specific sequences that may enhance the activity or confer tissue specific activity. For example, the maize SGB6 gene core promoter consists of about 37 nucleotides 5' of the transcriptional start site of the SGB6 gene, while the Cauliflower Mosaic Virus (CaMV) 35S core promoter consists of about 33 nucleotides 5' of the transcriptional start site of the 35S genome.

The maize INVINH1 promoter sequence of the present invention, when assembled within a DNA construct such that the promoter is operably linked to a polynucleotide of interest, enables expression of the operably linked polynucleotide in the cells of a plant stably transformed with this DNA construct. By "operably linked" is intended that the transcription or translation of the polynucleotide of interest is under the influence of the promoter sequence. In this manner, the promoters of the invention are provided in expression cassettes along with the polynucleotide of interest, typically a heterologous polynucleotide, for expression in the plant of interest. By "heterologous nucleotide sequence" or "heterologous polynucleotide" is intended a polynucleotide that is not naturally operably linked with the promoter sequence. While this polynucleotide is heterologous to the promoter, it may be homologous, or native, or heterologous, or foreign, to the plant host.

While a "nucleotide sequence" or "coding sequence" or "sequence" is the written code which describes and identifies a "polynucleotide" or "nucleic acid", the terms are sometimes used interchangeably.

A polynucleotide may be single- or double-stranded, depending on the context, and one of skill in the art would recognize which construction of the term is appropriate.

It is recognized that the INVINH1 promoter sequence of the invention may also be used with its native INVINH1 coding sequence to genetically engineer plants having an altered seed phenotype. A DNA construct comprising the INVINH1 promoter operably linked with its native INVINH1 coding sequence may be used to transform any plant of interest to bring about a change in seed phenotype. Where the promoter and its native coding sequence are naturally occurring within a plant, i.e., in maize, transformation of the plant with these operably linked sequences may result in a change in seed phenotype, as insertion of these operably linked sequences within a different region of the chromosomes alters the plant's genome.

The regulatory sequences of the present invention can be operably linked to a polynucleotide of interest and stably incorporated into the plant genome to drive "ESR-preferred" or "ESR-selective" expression of the operably linked polynucleotide. By "ESR-preferred" or "ESR-selective" is intended that expression of the operably linked polynucleotide is selective to the ESR, i.e., expression is most abundant in the ESR. "Selectively expressed" as used herein is intended as meaning that a gene is expressed in a tissue-preferred or tissue-selective manner. Therefore, the phrase "selectively expressed in the ESR" is intended as indicating that expression occurs in an ESR-preferred or ESR-selective manner. By "ESR" is intended that portion of the cereal endosperm that comprises the cytoplasmically dense cells surrounding the embryo. In "ESR-preferred" expression it is recognized that, although expression occurs most abundantly in the ESR, some level of expression of the operably linked polynucleotide may occur in other plant tissue types. In view of this expression pattern, the maize INVINH1 promoter, and variant and functional fragments thereof, are referred to herein as ESR-preferred promoters.

Modifications of the isolated promoter sequences of the present invention can provide for a range of expression of the operably linked polynucleotide of interest. Thus, they may be modified to be weak promoters or strong promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts.

Fragments and variants of the disclosed maize INVINH1 promoter sequence are also encompassed by the present invention. By "fragment" is intended a portion of the promoter sequence. Fragments of a promoter sequence may retain biological activity and hence encompass fragments capable of driving ESR-preferred expression of an operably linked polynucleotide. Thus, for example, less than the entire promoter sequence disclosed herein may be utilized to drive expression of an operably linked polynucleotide of interest, such as a polynucleotide encoding a heterologous protein. For example, Zhu et al. ((1995) *The Plant Cell* 7:1681-89) constructed a promoter sequence active in driving expression in which the 5' portion of the promoter up to the TATA box near the transcription start site was deleted. It is within skill in the art to determine whether such fragments decrease expression levels or alter the nature of expression, i.e., decrease or alter ESR-preferred expression. Alternatively, fragments of a promoter nucleotide sequence that are useful as hybridization probes, such as described below, generally do not retain this regulatory activity. Thus, fragments of a nucleotide sequence may range from at least about 20 nucleotides, about 50 nucleotides, about 100 nucleotides, and up to the full-length nucleotide sequence of the invention.

Thus, a fragment of the INVINH1 promoter nucleotide sequence of the invention may encode a biologically active portion of this promoter, or it may be a fragment that can be used as a hybridization probe or PCR primer using methods disclosed below. A biologically active portion of the promoter nucleotide sequence of the invention can be prepared by isolating a portion of one of the promoter nucleotide sequences disclosed herein and assessing the promoter activity of that sequence. Nucleic acid molecules that are fragments of a promoter nucleotide sequence will comprise at least 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, or up to the number of nucleotides present in the full-length promoter nucleotide sequence disclosed herein (i.e., 590 nucleotides for SEQ ID NO:1). Such fragments may be obtained as a sequence of the desired length derived from any region of the promoter sequences of the invention. Alternatively, fragments may be obtained from particular regions of the promoters of the invention, for example regions known to contain promoter elements of interest. Regions of interest contemplated in the present invention include about nucleotides 1-50, about nucleotides 51-100, about nucleotides 101-150, about nucleotides 151-200, about nucleotides 201-250, about nucleotides 251-300, about nucleotides 301-350, about nucleotides 351-400, about nucleotides 401-450, about nucleotides 451-500, about nucleotides 501-550, and about nucleotides 551-590.

The nucleotide sequences of such fragments will comprise one or more promoter elements of the particular promoter sequence of the invention, for example the TATA recognition sequence, the CAAT box, or upstream promoter elements. Such elements may be defined functionally, for example using promoter assays described elsewhere herein to identify such elements in mutants or fragments of the promoter sequences of the invention. Alternatively, such elements may be defined by sequence comparisons against general databases of characterized promoter elements, e.g. by the methods described in Higo et al. (1999) *Nucl. Acids. Res.* 27(1):297-300.

The promoter sequence of SEQ ID NO:1, for example, can be shown by such analysis to contain three cytokinin response elements (GGATT) corresponding to nucleotide positions 135-139, 274-278 and 552-556 of SEQ ID NO:1. See, for example, Sakai et al. (2000) *Plant J.* 24(6):703-711.

Such sequence comparisons can also be specifically made against ESR-preferred promoter sequences, for example the ESR-preferred promoters described in Bonello et al. (2000) *Gene* 219-227, herein incorporated by reference. See also WO 01/25439 and WO 02/36788, both of which are similarly incorporated by reference herein. Thus Bonello et al. identified a number of promoter elements in the ESR-preferred promoters they characterized, including the cereal amylase box (TATCCAT), maize P binding site (CCWACC), *B. napus* E-box (CANNTG), CMT box, root motif (ATAAAT), GT1 box (GRWMW), and a conspicuous CTACACCA element present in a tandem repeat close to each open reading frame.

Of these elements, SEQ ID NO:1 contains two GT1 box sequences at nucleotide positions 248-253 (GAAAAA) and 447-452 (GATAAA). In addition, alignment of SEQ ID NO:1 with the sequences provided in Bonello et al. identifies two short regions of identity that are in roughly the same location in each sequence relative to the ATG transcriptional start site: AGCATA and TAAAAAT, at positions 412-417 and 449-455 of SEQ ID NO:1, respectively.

However, the conserved CTACACCA element of Bonello et al. does not appear in SEQ ID NO: 1. Also, the cytokinin-responsive element (GGATT) which appears three times in SEQ ID NO: 1 is not present in the ESR-preferred promoters identified by Bonello et al.

Promoter elements defined by methods such as those described above will have utility in a variety of applications. In general, promoter elements identified in the promoters of the invention may be used to modulate the activity of other promoters, whether naturally occurring or synthetic, or to modulate the tissue-or developmental-specificity of other promoters. As an example, one or more of these elements may be operably linked to a naturally occurring promoter in order to change or enhance the properties of the naturally occurring promoter. Alternatively, one or more of these elements may used as a component of a synthetic promoter sequence in order to confer particular properties of interest on that synthetic promoter. Methods for assaying the activity of isolated promoter elements are widely available and may be routinely performed, for example using promoter screening assays described elsewhere herein. Identification of promoter elements may also allow for the manipulation of a promoter to remove one or more of those elements, thereby modulating the activity or tissue-or developmental-specificity of that promoter. For example the ESR-preferred promoters of the invention may be altered to remove one or more of their component promoter elements, thereby modulating their activity or their developmental or ESR-preferred expression.

Fragments of the INVINH1 promoter nucleotide sequence of the invention may be obtained by use of restriction enzymes to cleave the naturally occurring promoter nucleotide sequence disclosed herein; by synthesizing a nucleotide sequence from the naturally occurring sequence of the promoter DNA sequence; or through the use of PCR technology. See particularly, Mullis et al. (1987) *Methods Enzymol.* 155:335-350, and Erlich, ed. (1989) PCR *Technology* (Stockton Press, New York). Variants of these promoter fragments, such as those resulting from site-directed mutagenesis, are also encompassed by the compositions of the present invention.

By "variants" is intended sequences having substantial similarity with a promoter sequence disclosed herein. For nucleotide sequences, naturally occurring variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least 40%, 50%, 60%, 65%, 70%, generally at least 75%, 80%, 85%, preferably at least 90%, 91%, 92%, 93%, 94%, 95%, 96%, 97%, and more preferably at least 98%, 99% or more sequence identity to that particular nucleotide sequence as determined by sequence alignment programs described elsewhere herein using default parameters.

Biologically active variants are also encompassed by the present invention. Biologically active variants include, for example, the native promoter sequence of the invention having one or more nucleotide substitutions, deletions, or insertions that do not destroy promoter activity. The skilled artisan would know that such variants can be made systematically, for example by utilizing information regarding promoter elements obtained by any of the methods described previously to predict which changes to the sequence can be made without eliminating the promoter biological activity. Alternatively, promoter screening methods can be used to assay variant sequences in a routine fashion to determine which variants retain promoter function. Such techniques can be used to screen promoter sequences that have been randomly varied; alternatively, they can be used to screen promoter sequences that have been varied on the basis of the knowledge of promoter elements discussed above.

Promoter activity for any of the variants, fragments, or other nucleotide sequences of the invention may be assayed using a variety of techniques well known to one of ordinary skill in the art, including, for example, Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Plainview, N.Y.), herein incorporated by reference. Alternatively, promoter assays may be based on the measurement of levels of a reporter gene such as green fluorescent protein (GFP) or the like produced under the control of a promoter fragment or variant. See, for example, U.S. Pat. No. 6,072,050, herein incorporated by reference. Variants, fragments, or other nucleotide sequences of the invention may be routinely assayed for activity using such assays; for example, large collections of randomly generated fragments may be quickly and routinely screened for promoter activity using these or other methods. In the instant case, for example, such assays might include the use of the promoters of the invention to drive the expression of the GUS reporter gene, as well as the cytokinin producing gene, isopentenyl transferase (IPT).

Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the maize INVINH1 promoter sequence set forth herein. Sequences isolated based on their sequence identity to the entire INVINH1 promoter sequence set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the INVINH1 promoter sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire INVINH1 promoter sequence disclosed herein, or one or more portions thereof, may be used as a probe capable of specifically hybridizing to corresponding INVINH1 promoter sequences. To achieve specific hybridization under a variety of conditions, such probes include sequences that are unique among INVINH1 promoter sequences and are preferably at least about 10 nucleotides in length, and most preferably at least about 20 nucleotides in length. Such probes may be used to amplify corresponding INVINH1 promoter sequences from a chosen plant by PCR. This technique may be used to isolate additional promoter sequences from a desired plant or as a diagnostic assay to determine the presence of additional promoter sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5×to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that have ESR-preferred promoter activity and which hybridize under stringent conditions to the INVINH1 promoter sequence disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BESTFIT program provides an optimal alignment of the best segment of similarity between two sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. BLASTX may utilize the BLOSUM62 scoring matrix. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. More information is available from the National Center for Biotechnology Information, U.S. National Library of Medicine, 8600 Rockville Pike, Bethesda, Md. 20894. Alignment may also be performed manually by inspection.

Unless otherwise stated, sequence identity values provided herein refer to the value obtained using GAP version 10 using the following parameters: % identity using GAP Weight (gap creation penalty) of 50 and Length Weight (gap extension penalty) of 3; % similarity using Gap Weight of 12 and Length Weight of 4, or any equivalent program. By "equivalent program" is intended any sequence comparison program that, for any two sequences in question, generates an alignment having identical nucleotide matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid sequences makes reference to the bases in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90%, and most preferably at least 95% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein.

The promoter sequences disclosed herein are useful for driving expression of polynucleotides of interest in order to vary the phenotype of a plant, particularly the phenotype of plant seeds. Various changes in seed phenotype are of interest, including modifying expression of a polynucleotide in a plant ESR, altering a plant's pathogen or insect defense mechanism, increasing the plant's tolerance to herbicides, altering ESR development to respond to environmental stress, and the like. These results can be achieved by providing expression of exogenous products, or increasing expression of endogenous products, in plant seeds. Alternatively, the results can be achieved by providing for a reduction of expression of one or more endogenous products, particularly enzymes, transporters, or cofactors in the seed. These modifications result in a change in phenotype of the transformed seed. Various other changes in seed phenotype are of interest including modifying the fatty acid composition in a seed, altering the amino acid content of a seed, altering a plant's pathogen defense mechanism to improve seed yield, and the like. It is recognized that any gene of interest, including the native INVINH1 coding sequence, can be operably linked to a promoter of the invention for expression in the seed of a transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increases, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine- and sulfur-containing amino acids, thereby providing essential amino acids, and also modifications of the amount and/or types of starch contained in the seed. Hordothionin protein modifications are described in U.S. Pat. Nos. 5,703,049, 5,885,801, 5,885,802, and 5,990,389, herein incorporated by reference. Other examples are lysine-and/or sulfur-rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

In one embodiment, the promoter of the present invention modulates genes encoding proteins that act as cell cycle regulators, or that control carbohydrate metabolism or phytohormone levels, as has been shown in tobacco and canola with other tissue-preferred promoters (Ma et al. (1998) *Australian J. Plant Physio.* 25(1):53-59; Roeckel et al. (1997) *Transgenic Res.* 6(2):133-141.) Other examples of genes of interest include regulators of cell division, such as a cytokinin biosynthesis gene, for example, isopentenyl transferase. Greater cell division in the ESR through expression of cytokinin biosynthesis genes may result in larger seeds or create a larger sink for photosynthate to buffer seed development during transient abiotic stress. Alternatively, the promoters of the invention could be used to drive expression of a toxic or deleterious gene product (e.g., DAM methylase from *E. coli*) to reduce or impede embryo development. Also, expression of endogenous or heterologous nucleotides under the direction of the promoter may result in maintenance of a desirable seed phenotype that might otherwise be altered under adverse environmental conditions.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Agronomic traits in seeds can be improved by altering expression of genes that affect the response of seed growth and development during environmental stress (Cheikh-N et al. (1994) *Plant Physiol.* 106(1):45-5), and genes controlling carbohydrate metabolism to reduce seed abortion in maize (Zinselmeier et al. (1995) *Plant Physiol.* 107(2):385-391).

Insect resistance genes may encode resistance to pests such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonisin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) *J. Bacteriol.* 170:5837-5847) facilitate expression of polyhydroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant seed, can be increased. This is achieved by the expression of such proteins having enhanced amino acid content.

The nucleotide sequence of interest operably linked to a promoter of the invention may be an antisense DNA nucleotide sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the transformed plant seed, particularly in the ESR of the transformed plant seed.

In one embodiment of the invention, expression cassettes will comprise a transcriptional initiation region comprising the maize INVINH1 promoter nucleotide sequence disclosed herein, or variants or fragments thereof, operably linked to a polynucleotide of interest whose expression is to be controlled by this ESR-preferred promoter. Such an expression cassette is provided with a plurality of restriction sites for insertion of the nucleotide sequence to be under the transcriptional regulation of the regulatory regions. The expression cassette may additionally contain selectable marker genes.

The expression cassette may include in the 5'-to-3' direction of transcription, a transcriptional and translational initiation region (i.e., an ESR-preferred promoter described herein), a polynucleotide of interest, and a transcriptional and translational termination region (i.e., termination region) functional in plants. The polynucleotide of interest generally is heterologous (i.e., not naturally occurring with the INVINH1 promoter sequence) to the promoter sequence, although the native coding sequence can be used in the expression cassette. The termination region may be native with the transcriptional initiation region comprising the promoter of the present invention, may be native with the polynucleotide of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassette comprising a promoter sequence of the present invention operably linked to a polynucleotide of interest may also contain at least one additional nucleotide sequence for a gene to be cotransformed into the organism. Alternatively, the additional sequence(s) can be provided on another expression cassette.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986)); MDMV leader (Maize Dwarf Mosaic Virus) (*Virology* 154:9-20); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) *Molecular Biology of RNA*, pages 237-256); and maize chlorotic mottle virus leader (MCMV) (Lommel et al. (1991) *Virology* 81:382-385). See also Della-Cioppa et al. (1987) *Plant Physiology* 84:965-968. Other methods known to enhance translation and/or mRNA stability can also be utilized, for example, introns, and the like.

It is recognized that to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al., (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481); phosphinothricin (DeBlock et al. (1987) *EMBO J.* 6:2513-2518).

Other genes that are useful in the recovery of transgenic events but might not be required in the final product would include, but are not limited to, GUS (b-glucoronidase; Jefferson (1987) *Plant Mol. Biol. Rep.* 5:387), GFP (green fluorescence protein; Chalfie et al. (1994) *Science* 263:802), luciferase (Riggs et al. (1987) *Nucleic Acids Res.* 15(19): 8115 and Luehrsen et al. (1992) *Methods Enzymol.* 216:397-414), and the maize genes encoding for anthocyanin production (Ludwig et al. (1990) *Science* 247:449).

The nucleic acid molecules of the present invention are useful in methods directed to expressing a nucleotide sequence in a plant. This may be accomplished by transforming a plant cell of interest with an expression cassette comprising a promoter identified herein, operably linked to the polynucleotide of interest, and regenerating a stably transformed plant from the plant cell. The methods of the invention are also directed to selectively expressing a polynucleotide of interest in the ESR of seed of a plant. These methods comprise transforming a plant cell with an expression cassette comprising a promoter identified herein that initiates ESR-preferred transcription, operably linked to the nucleotide sequence of interest, and regenerating a transformed plant from said plant cell, whereby the nucleotide sequence of interest is expressed in transformed seeds of this plant.

The expression cassette comprising the particular promoter sequence of the present invention operably linked to a nucleotide sequence of interest can be used to transform any plant. In this manner, genetically modified plants, plant cells, plant tissue, seed, ESR, and the like can be obtained.

In certain embodiments the nucleic acid sequences of the present invention can be stacked with any combination of polynucleotide sequences of interest in order to create plants with a desired phenotype. The combinations generated can also include multiple copies of any one of the polynucleotides of interest. The polynucleotides of the present invention can also be stacked with a gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. Provisional Application Serial No. 60/246,455, filed Nov. 11, 2000); and thioredoxins (U.S. Provisional Application Serial No. 60/250,705, filed Dec. 12, 2000)), the disclosures of which are herein incorporated by reference. The polynucleotides of the present invention can also be stacked with traits desirable for insect, disease or herbicide resistance (e.g. *Bacillus thuringiensis* toxic proteins (U.S. Pat. Nos. 5,366,892; 5,747,450; 5,737,514; 5,723,756; 5,593,881; Geiser et al (1986) *Gene* 48:109); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotil*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be further grown, and pollinated with either the same transformed strain or different strains, and the resulting plant having ESR-preferred expression of the desired phenotypic characteristic identified. Two or more generations may be grown to ensure that ESR-preferred expression of the desired phenotypic characteristic is stably maintained and inherited and then seeds harvested to ensure ESR-preferred expression of the desired phenotypic characteristic has been achieved. Thus as used herein, "transformed seeds" refers to seeds that contain the nucleotide construct stably integrated into the plant genome.

The invention provides compositions for screening compounds that modulate expression within the ESR of embryos and plants. The vectors, cells, and plants can be used for screening candidate molecules for agonists and antagonists of the promoters of the invention. For example, a reporter gene can be operably linked to a promoter of the invention and expressed as a transgene in a plant. Compounds to be tested are added and reporter gene expression is measured to determine the effect on promoter activity.

The following examples are offered by way of illustration and not by way of limitation.

EXPERIMENTAL

EXAMPLE 1

Isolation of the ESR-preferred Promoter of INVINH1

The INVINH1 nucleotide sequence encoding the maize invertase inhibitor gene INVINH1 was isolated and characterized as described in co-pending U.S. patent application Ser. No. 09/780,717, filed Feb. 9, 2001. When the mRNA expression of this gene was determined by in situ analysis, it was discovered that expression is ESR-preferred, as is shown in FIG. 1. The ESR-preferred expression of the INVINH1 protein suggests that it may have additional roles in plant development in addition to its role as an invertase inhibitor, since a number of small proteins with very localized expression patterns have been shown in a range of species to be important signaling molecules and/or ligands for developmentally important receptors. For example, the Clavata3 proteins have been shown to be important for meristem identity in plants. Additionally, there is precedent in the mammalian literature for small proteins acting as both enzyme inhibitors and signaling molecules; Blastokinin/

Clara2/uteroglobin, for example, acts as an inhibitor of phospholipase A2 as well as a cytokine-like signaling molecule. See Mukherjee et al. (1999) Cell Mol. Life Sci. 55:771-787.

To isolate upstream regulatory regions from the INVINH1 gene, a commercially available "Universal Genome Walker" kit obtained from Clontech (Palo Alto, Calif.) was used. INVINH1-specific anti-sense primers were designed to the coding sequence of INVINH1 (AACTTGATGCAGTAG-GCGTAGCCGGTGTCC (SEQ ID NO:2) and CTTGTAG-GACGGAAGCGTTGGACGTGGAGC (SEQ ID NO:3). Three rounds of amplification were performed with gene specific primers and primers provided in the kit.

In Situ Analysis

Greenhouse grown inbred maize (public inbred B73) was grown in a greenhouse in Johnston, Iowa, USA. Kernels were taken from the middle of ears harvested at 5 DAP. Longitudinal median sections containing embryos were obtained and immediately fixed in 3.7% paraformaldehyde and 0.2% picric acid in 50 mM potassium phosphate and 5 mM EGTA buffer, pH 6.8, which was prepared in diethyl pyrocarbonate-treated deionized, distilled water (DEPC-dd$H_2O$). Fixation, sectioning and in situ conditions were as published previously (Woo et al. (2001) Plant Cell 13(10): 2297-2317). DIG-labeled sense and antisense RNA probes were synthesized in vitro by transcription of linearized pBluescript II KS+ plasmids containing the cDNA of interest with T3 or T7 RNA polymerase (Roche Molecular Biochemicals). For ZmINVINH1 a HindIII/SmaI fragment was used to reduce non-specific binding from the polyA sequence present in the cDNA. After hybridization, slides were washed twice for 1 hr at 63° C. with 0.2×SSC (1×SSC is 0.15 M NaCl and 0.015 M sodium citrate) containing 0.05% SDS. Between these stringent washes, the slides were treated with 10 µg/mL RNase A for 30 min at 37° C. DIG-labeled probes were detected with anti-DIG antibody conjugated with AP and an AP color reaction using the Fast Red TR/Naphthol AS-MX system (Sigma, St. Louis, Mo.), which produces a red precipitate.

EXAMPLE 2

Transformation and Regeneration of Transgenic Plants

Immature maize embryos from greenhouse donor plants are bombarded with a plasmid containing the ESR-preferred promoter of the invention operably linked to a gene of interest and the selectable marker gene PAT (Wohileben et al. (1988) Gene 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% CLOROX® chlorine bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector is made comprising the ESR-preferred promoter of the invention operably linked to a polynucleotide of interest. This plasmid DNA plus plasmid DNA containing a PAT selectable marker is precipitated onto 1.1 µm (average diameter) tungsten pellets using a $CaCl_2$ precipitation procedure as follows:

100 µl prepared tungsten particles in water
  10 µl (1 µg) DNA in Tris EDTA buffer (1 µg total DNA)
  100 µl 2.5 M $CaCl_2$
  10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Following generation of mature $T_0$ plants, promoter analysis is conducted on $T_1$ seed collected from $T_0$ plants. Immature seeds from $T_0$ plants are collected at specific intervals after pollination, starting 2 days after pollination (DAP) and extending to physiological maturity. Each seed is dissected vertically from silk scar to pedicel and examined for tissue and temporal expression of the transgene product, and hence specificity of the promoter activity. Silks, husks, leaves, tassels, and roots are also collected and examined for the presence or absence of expression of the transgene product. The temporal and tissue specificity of the promoter is confirmed in the $T_2$ generation.

Bombardment and Culture Media

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l GELRITE® agar substitute (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I H2O following adjustment to pH 5.8 with KOH); 3.0 g/l GELRITE® agar substitute (added after bringing to volume with D-I H$_2$O); and 0.85 mg/l silver nitrate and 3.0 mg/l bialaphos(both added after sterilizing the medium and cooling to room temperature).

EXAMPLE 3

Agrobacterium-mediated Transformation

For *Agrobacterium*-mediated transformation of maize with the ESR-preferred promoter of the invention, preferably the method of Zhao is employed (U.S. Pat. No. 5,981,840, and PCT patent publication WO98/32326, the contents of which are hereby incorporated by reference). Briefly, immature embryos are isolated from maize and the embryos contacted with a suspension of *Agrobacterium*, where the bacteria are capable of transferring the DNA construct of interest to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Temporal and tissue specificity of the promoter is examined as described in Example 2 above.

EXAMPLE 4

Soybean Embryo Transformation Prophetic Example soybean embryos are bombarded with a plasmid containing the ESR-preferred promoter of the invention operably linked to a polynucleotide of interest, as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the $^{35}$S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the ESR-preferred promoter of the invention operably linked to a polynucleotide of interest can be isolated as a restriction fragment. This fragment can then be inserted into a unique restriction site of the vector carrying the marker gene.

To 50 µl of a 60 mg/ml 1 µm gold particle suspension are added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos. Temporal and tissue specificity of the promoter is examined by monitoring expression of the transgene product during plant and seed development.

EXAMPLE 5

Sunflower Meristem Tissue Transformation Prophetic Example

Sunflower meristem tissues are transformed with an expression cassette containing the ESR-preferred promoter of the invention operably linked to a gene of interest as follows (see also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% CLOROX® chlorine bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473-497), Shepard's vitamin additions (Shepard (1980) in *Emergent Techniques for the Genetic Improvement of Crops*, University of Minn. Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) Plant Mol. Biol. 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ESR-preferred promoter of the invention operably linked to a polynucleotide of interest is introduced into *Agrobacterium* strain EHA105 via freeze-thawing as described by Holsters et al. (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% GELRITE® agar substitute, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by activity analysis of leaf extracts while transgenic seeds harvested from NPTII-positive $T_0$ plants are identified by activity analysis of small portions of dry seed cotyledon.

All publications and patent applications mentioned in the specification are indicative of the level of skill in the art of those to whom this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated nucleic acid molecule comprising a polynucleotide which initiates transcription in a plant cell and comprises the sequence of SEQ ID NO: 1.

2. An expression cassette comprising the nucleic acid molecule of claim 1 operably linked to a polynucleotide of interest.

3. A vector comprising the expression cassette of claim 2.

4. A plant cell having stably incorporated into its genome the expression cassette of claim 2.

5. The plant cell of claim 4, wherein said plant cell is from a monocot.

6. The plant cell of claim 5, wherein said monocot is maize, barley, wheat, oat, rye, sorghum, or rice.

7. A plant having stably incorporated into its genome the expression cassette of claim 2.

8. The plant of claim 7, wherein said plant is a monocot.

9. The plant of claim 8, wherein said monocot is maize, barley, wheat, oat, rye, sorghum, or rice.

10. A seed comprising the expression cassette of claim 2.

11. The plant of claim 7, wherein the polynucleotide of interest encodes a gene product that confers pathogen or insect resistance.

12. The plant of claim 7, wherein the polynucleotide of interest encodes a polypeptide involved in cell cycle regulation, carbohydrate metabolism, protein metabolism, fatty acid metabolism, or phytohormone biosynthesis.

13. A method for expressing a first polynucleotide in a plant, said method comprising introducing into a plant an expression cassette comprising a promoter and a first polynucleotide operably linked thereto, wherein said promoter comprises a second polynucleotide that initiates transcription of an operably linked polynucleotide in a plant cell, and wherein said second polynucleotide comprises SEQ ID NO: 1.

14. The method of claim 13, wherein said plant is a monocot.

15. The method of claim 14, wherein said plant is a monocot is maize, barley, wheat, oat, rye, sorghum, or rice.

16. The method of claim 13, wherein said first polynucleotide encodes a gene product that confers pathogen or insect resistance.

17. The method of claim 13, wherein said first polynucleotide encodes a polypeptide involved in cell cycle regulation, carbohydrate metabolism, protein metabolism, fatty acid metabolism, or phytohormone biosynthesis.

18. A method for expressing a first polynucleotide in a plant cell, said method comprising introducing into a plant cell an expression cassette comprising a promoter and a first polynucleotide operably linked thereto, wherein said promoter comprises a second polynucleotide that initiates transcription of an operably linked polynucleotide in a plant cell, and wherein said second polynuceotide comprises SEQ ID NO:1.

19. The method of claim 18, wherein said plant cell is from a monocot.

20. The method of claim 19, wherein said monocot is maize, barley, wheat, oat, rye, sorghum, or rice.

21. The method of claim 18, wherein said first polynucleotide encodes a gene product that confers pathogen or insect resistance.

22. The method of claim 18, wherein said first polynucleotide encodes a polypeptide involved in cell cycle regulation, cabohydrate metabolism, protein metabolism, fatty acid metabolism, or phytohormone biosynthesis.

23. A method for selectively expressing a first polynucleotide in the embryo surrounding region (ESR) of a plant seed, said method comprising introducing into a plant an expression cassette comprising a promoter and a first polynucleotide operably linked thereto, wherein said promoter comprises a second polynucleotide that initiates transcription of an operably linked polynucleotide in the ESR of a plant seed, and wherein said second polynucleotide comprises SEQ ID NO:1.

24. The method of claim 23, wherein expression of said first polynucleotide alters the phenotype of said transformed seed.

25. The method of claim 23, wherein the plant is a monoct.

26. The method of claim 25, wherein the monocto is maize, barley, wheat, oat, rey, sorghum, or rice.

27. The method of claim 23, wherein the first polynucleotide encodes a gene product that confers pathogen or insect resistance.

28. The method of claim 23, wherein the first polynucleotide encodes a polypeptide involved in cell cycle regulation, carbohydrate metabolism, protein metabolism, fatty acid metabolism, or phytohormone biosynthesis.

29. A method of altering plant phenotype comprising:
(a) transforming a plant host cell with at least one isolated nucleic acid molecule of claim 1 operably linked to at least one polynucleotide of interest;
(b) growing the transformed host cell under conditions favoring plant regeneration; and
(c) generating a plant wherein said regenerated plant exhibits an altered phenotype.

* * * * *